US00PP09716P

United States Patent [19]

Olesen et al.

[11] Patent Number: Plant 9,716

[45] Date of Patent: Dec. 3, 1996

[54] MINIATURE ROSE PLANT NAMED 'POULSUN'

[75] Inventors: Morgens N. Olesen; Pernille Olesen, both of Fredensborg, Denmark

[73] Assignee: Bear Creek Gardens, Inc., Medford, Oreg.

[21] Appl. No.: 590,263

[22] Filed: Jan. 19, 1996

[51] Int. Cl.[6] ..... A01H 5/00

[52] U.S. Cl. ..... Plt./8.2

[58] Field of Search ..... Plt./8.2

*Primary Examiner*—Howard J. Locker

*Attorney, Agent, or Firm*—Klarquist Sparkman Campbell Leigh & Whinston

[57] ABSTRACT

A miniature rose plant having bright yellow flowers, dark green, glossy foliage, resistance to rust and powdery mildew, compact, even growth, and which is easily propogated from cuttings.

1 Drawing Sheet

The present invention relates to a new and distinct variety of rose plant of the miniature class which was originated by our crossing an unnamed seedling, unpatented, with the variety Goldmarie 82, unpatented.

The primary objective of this breeding was to produce a new rose variety having the compact habit, vigor and small flower size of the female miniature rose combined with the glossy foliage, health and bright yellow flower color of the male floribunda parent. The objective was substantially achieved, along with other desirable improvements, as evidenced by the following unique combination of characteristics that are outstanding in the new variety and that distinguish it from its parents, as well as from all other varieties of which I am aware:

1. Bright yellow flowers;
2. Dark green glossy foliage;
3. Compact even growth habit;
4. Vigorous growth from softwood cuttings; and
5. Resistance to powdery mildew and rust.

Asexual reproduction of this new variety by softwood cuttings, as performed at Somis, Calif., and Fredensborg, Denmark, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Goldmarie 82.

Classification:

*Botanical.*—*Rosa hybrida.*

*Commercial.*—Miniature.

Flower

Observations made from specimens grown in a greenhouse environment at Somis, Calif., in 1994–1995.

Blooming habit: Continuous.

Bud:

*Size.*—¾ inch long when the petals start to unfurl.

*Form.*—The bud form is long and pointed ovoid.

*Color.*—When sepals first divide, bud color is Yellow Group 13A. When half blown, the upper sides of the petals are Yellow Group 13A; and the lower sides of the petals are Yellow Group 13B.

*Sepals.*—Color: Green Group 138B. Surface texture: Covered in fine hairs. There are three normally appendaged sepals. There are two unappendaged sepals with smooth edges and occasional glands.

*Receptacle.*—Color: Green Group 137D. Shape: Apple. Size: Small (¼ inch×¼ inch). Surface: Smooth.

*Peduncle.*—Length: Short (1½ inches to 2 inches). Surface: Glandular. Color: Medium green. Strength: Stiff, erect and slender.

Bloom:

*Size.*—Small. Average open size is 2 inches to 2½ inches.

*Borne.*—Singly and several together, in pyramidal clusters.

*Stems.*—Short and strong. Average length is about 4 inches to 6 inches).

*Form.*—When first open: Cupped. Permanence: Retains its form to the end.

*Petalage.*—Number of petals under normal conditions: 30 to 35.

*Color.*—The upper side of the petals is Yellow Group 13A. The reverse side of the petals is Yellow Group 13B. No distinctive marking at the petal base. The major color on the upper side is Yellow Group 13A.

*Variegations.*—Occasional green streak on guard petals.

*Discoloration.*—The general tonality at the end of the first day: No change. At the end of the third day: No change. By day 4 or 5, there is a general fading to Yellow Group 13C. Finally, by day 6, flowers fade to Yellow Group 13D.

*Fragrance.*—Slight.

Petals:

*Texture.*—Thick.

*Shape.*—Round with a small tip or point at the apex of the petal.

*Form.*—Flat.

*Arrangement.*—Imbricated, with few, small petaloids in the center.

*Persistence.*—Drop off cleanly.

*Lastingness.*—On the plant: Long (6 days). As a cut flower: Not tested.

Reproductive parts:

*Anthers.*—Size: Medium. Quantity: Many. Color: Yellow. Arrangement: Regular around styles mixed with a few petaloids.

*Filaments.*—Color: Yellow.

*Pollen.*—Color: Gold yellow.

*Styles.*—Color: Greenish white.

*Stigmas.*—Color: Greenish white.

Form: Bush.

Growth: Vigorous, dwarf, upright, branching, and compact. Saleable plant 10 inches to 12 inches above pot lip.

Foliage:

*Number of leaflets on normal mid-stem leaves.*—5 or 7.

*Size.*—Small (3½ inches long by 2 inches wide).

*Quantity.*—Abundant.

*Color.*—New and old foliage: Top Green Group 137A/reverse 137C.

Leaflets:

*Shape.*—Pointed oval.

*Texture.*—Upper side: Glossy and smooth.

*Edge.*—Serrated.

*Serration.*—Single, small.

*Petiole rachis.*—Color: Green.

*Petiole underside.*—Rough, with prickles.

*Stipules.*—Long, bearded and glandular.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short (¼ inch), hooked downward.

*Color when young.*—Green with some red at the place of attachment to the stem.

Small prickles:

*Quantity.*—On main stalks: None. On laterals: None.

We claim:

1. A new and distinct variety of rose plant of the miniature class, substantially as herein shown and described, characterized particularly as to novelty by the unique combination of its bright yellow flowers, its dark green, glossy foliage, its resistance to rust and powdery mildew, its ease of propagation from softwood cuttings, and its compact, even growth.

* * * * *

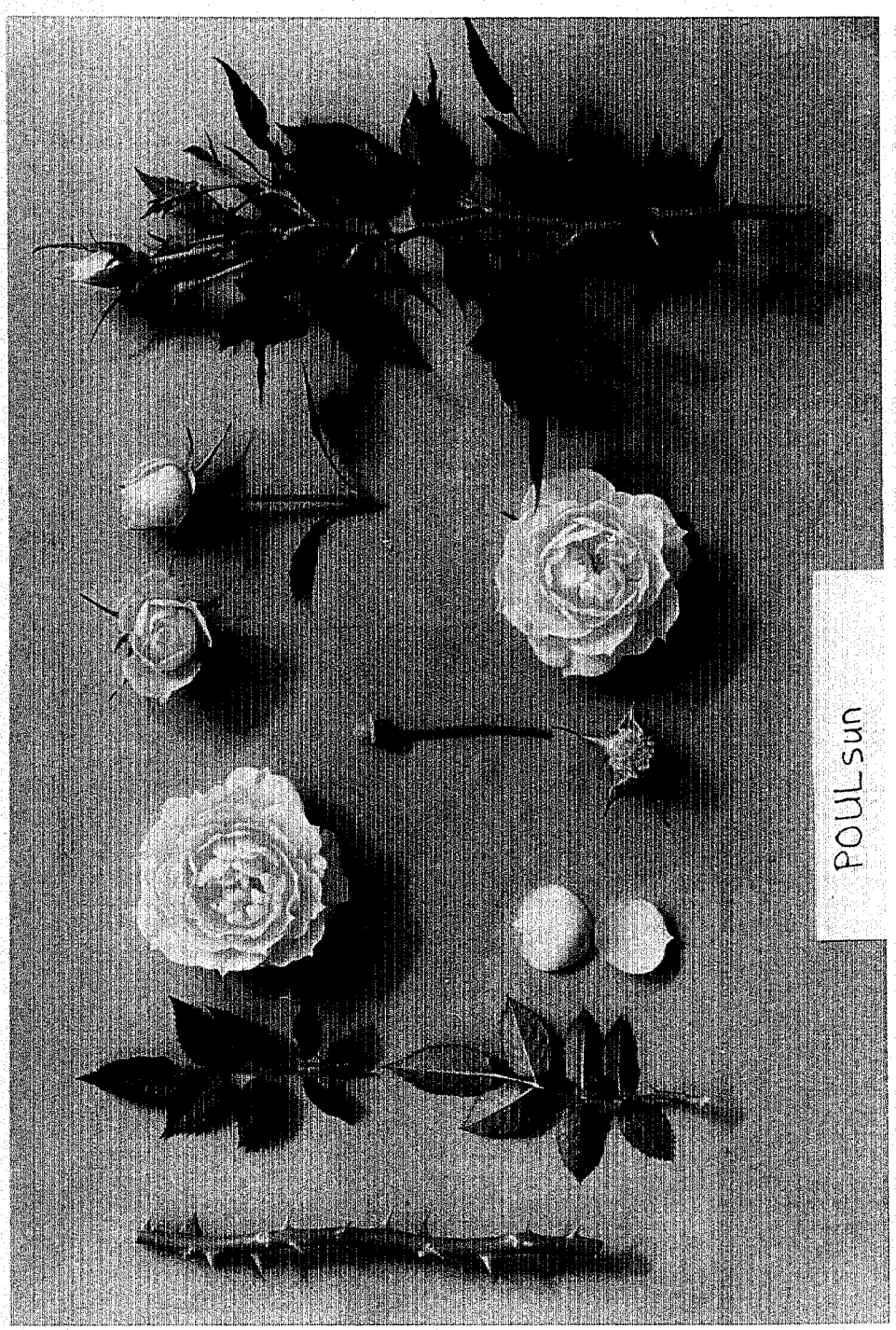
POULsun